United States Patent
Katz

(10) Patent No.: US 9,033,858 B2
(45) Date of Patent: May 19, 2015

(54) METHOD AND APPARATUS FOR CONCENTRATING PLATELETS FROM PLATELET-RICH PLASMA

(71) Applicant: Fenwal, Inc., Lake Zurich, IL (US)

(72) Inventor: Steven R. Katz, Deerfield, IL (US)

(73) Assignee: Fenwal, Inc., Lake Zurich, IL (US)

( * ) Notice: Subject to any disclaimer, the term of this patent is extended or adjusted under 35 U.S.C. 154(b) by 363 days.

(21) Appl. No.: 13/726,703

(22) Filed: Dec. 26, 2012

(65) Prior Publication Data
US 2013/0203582 A1    Aug. 8, 2013

Related U.S. Application Data

(60) Provisional application No. 61/594,066, filed on Feb. 2, 2012.

(51) Int. Cl.
| | |
|---|---|
| *B04B 5/04* | (2006.01) |
| *B04B 11/00* | (2006.01) |
| *B01D 21/26* | (2006.01) |
| *B01D 21/34* | (2006.01) |
| *A61M 1/36* | (2006.01) |

(52) U.S. Cl.
CPC ............... *B04B 11/00* (2013.01); *B04B 5/0442* (2013.01); *B04B 2005/0471* (2013.01); *A61M 1/3693* (2013.01); *A61M 2202/0427* (2013.01); *A61M 1/3696* (2014.02); *B01D 21/262* (2013.01); *B01D 21/34* (2013.01); *B01D 2221/10* (2013.01)

(58) Field of Classification Search
CPC ... A61M 1/3693; A61M 1/3696; A61M 1/38; B04B 5/0442; B04B 2005/0442; B04B 2005/045; B04B 2005/0471; B04B 2005/0492
See application file for complete search history.

(56) References Cited

U.S. PATENT DOCUMENTS

| | | |
|---|---|---|
| 5,674,173 A | 10/1997 | Hlavinka et al. |
| 5,722,926 A | 3/1998 | Hlavinka et al. |
| 5,906,570 A | 5/1999 | Langley et al. |
| 5,913,768 A | 6/1999 | Langley et al. |
| 5,939,319 A | 8/1999 | Hlavinka et al. |
| 5,951,877 A | 9/1999 | Langley et al. |
| 6,022,306 A | 2/2000 | Dumont et al. |
| 6,051,146 A | 4/2000 | Green et al. |
| 6,053,856 A | 4/2000 | Hlavinka |
| 6,071,422 A | 6/2000 | Hlavinka et al. |
| 6,334,842 B1 | 1/2002 | Hlavinka et al. |
| 2012/0316051 A1 * | 12/2012 | Holmes ........................ 494/42 |

* cited by examiner

*Primary Examiner* — Timothy Cleveland
(74) *Attorney, Agent, or Firm* — Cook Alex Ltd.

(57) ABSTRACT

An apparatus for use with a centrifugal cellular separation device that comprises a rotor rotatable about an axis of rotation is provided that comprises a fluid separation chamber having a first port, a second port spaced apart from the first port, and a third port located intermediate the first port and the second port. The fluid separation chamber has a cross sectional area generally transverse to a radius extending from the axis of rotation that varies between the first port and the second port. The fluid separation chamber is adapted to be mounted to the rotor so as to be rotatable therewith, with the first port located at a greater radial distance from the axis than the second port, and the third port located radially intermediate the first port and the second port.

5 Claims, 4 Drawing Sheets

METHOD AND APPARATUS FOR CONCENTRATING PLATELETS FROM PLATELET-RICH PLASMA

CROSS REFERENCE TO RELATED APPLICATION

This application claims the benefit of the filing date of U.S. Provisional Application Ser. No. 61/594,066, filed Feb. 2, 2012, the entire contents of which is incorporated by reference herein.

FIELD OF THE DISCLOSURE

The present application relates to the processing of blood components and, more particularly, to a method and apparatus for concentrating platelets from platelet-rich plasma.

BACKGROUND

Continuous blood cell separation and collection is a well-known process for collecting desired blood components, such as red cells, platelets or plasma from a donor. Typically whole blood is withdrawn from a donor and directed into a centrifugal processing chamber to separate the whole blood into its various therapeutic components. This is often carried out utilizing blood processing systems and methods comprising a durable centrifuge in association with a single-use, sterile fluid circuit that may include a processing chamber and associated storage containers, fluid flow tubing and the like. The processing chamber is usually mounted on a centrifuge rotor or bowl, which spins the chamber creating a centrifugal field, which separates the whole blood into its components based on their density.

Well-known and exemplary centrifugal blood processing systems include the Amicus® and Alyx® separators, available from Fenwal Inc. of Lake Zurich, Ill. The functional aspects of the Amicus® separator are disclosed in, e.g., U.S. Pat. Nos. 6,312,607 and 6,582,349, the entire disclosures of which are incorporated herein by reference.

In a centrifugal processing system such as the Amicus® separator, whole blood is typically separated into components in a two-stage process, using a belt-shaped processing container that has two separate processing chambers. The processing container is secured to a support in the form of a rotatable spool that is received within an outer bowl, such that the processing container is enclosed in an annular space between the spool and the bowl. The spool and bowl are rotated in unison about a common axis to centrifugally separate the whole blood into components. In the usual two-stage process for collecting platelets, whole blood is continuously separated into concentrated red blood cells (RBC) and platelet rich plasma (PRP) in the first separation chamber. The PRP is then directed to the second centrifuge chamber for separation into platelet concentrate (PC) and platelet reduced (or poor) plasma (PPP). The red cells and PPP are returned to the donor or stored in collection containers, and the platelet concentrate accumulates in the second chamber.

Under certain circumstances, it may be desirable to increase the concentration of the platelets in the platelet concentrate beyond that resulting from the second stage of the above-described process. This may be done by membrane filtration. Alternatively, further concentration of the platelets may be achieved by a process known as centrifugal elutriation.

Centrifugal elutriation is a method of separating cells suspended in a liquid medium by which a separation chamber is provided into which a liquid comprising cells suspended in a liquid medium is subjected to counteracting centrifugal and flow forces to create a fluidized bed of the cells within the separation chamber. After the fluidized bed is created, the smaller cells within the fluidized bed may then be drawn out of the separation chamber by introducing additional suspension into the chamber. As additional cells from the added suspension are introduced into the fluidized bed, an amount of the smaller cells is expelled from the fluidized bed into a separate collection receptacle.

By way of the present disclosure, an improved method and apparatus for concentrating platelets from platelet-rich plasma using centrifugal elutriation is provided.

SUMMARY OF THE DISCLOSURE

The present subject matter has a number of aspects which may be used in various combinations. The disclosure of one or more specific embodiments is for the purposes of disclosure and description, and not limitation. This summary only highlights a few of the aspects of the subject matter, and additional aspects are disclosed in the accompanying drawings and following detailed description.

By way of the present application, an apparatus for use with a centrifugal cellular separation device to provide for a concentrated blood component product is provided.

In keeping with a first aspect of the disclosure, the apparatus is for use with a centrifugal cellular separation device comprising a rotor that is rotatable about an axis of rotation. A fluid separation chamber is provided that has a first port comprising an inlet, a second port comprising a first outlet spaced apart from the inlet, and a third port comprising a second outlet located intermediate the inlet and the first outlet. The fluid separation chamber has a cross sectional area generally transverse to a radius extending from the axis of rotation that varies between the inlet and the first outlet. The fluid separation chamber is adapted to be mounted to the rotor so as to be rotatable therewith, with the inlet located at a greater radial distance from the axis than the first outlet, and the second outlet located radially intermediate the inlet and the first outlet.

In a further aspect of the disclosure, the cross sectional area of the fluid separation chamber has a maximum area at a radial location between the inlet and the first outlet.

In another aspect of the disclosure, a centrifugal cellular separation device is provided that comprises a rotor rotatable about an axis of rotation, and an apparatus as variously described above is removably secured to the rotor so as to be rotatable therewith, with the inlet and the first outlet aligned generally along a radius of the rotor through the axis of rotation, and the first outlet being positioned along the radius between the inlet and the axis of rotation.

In a further aspect of the disclosure, the rotor is durable and reusable, while the apparatus is disposable.

In another aspect of the disclosure, a method for separating a first type of cellular particles suspended in a liquid medium is provided by rotating a centrifugal rotor about an axis of rotation. The rotor includes a fluid separation chamber associated therewith that has a first port comprising an inlet, a second port comprising a first outlet spaced from the inlet, a third port comprising a second outlet intermediate the inlet and first outlet, and a cross-sectional area generally transverse to a radius of the rotor that varies between the inlet and the first outlet. The inlet of the fluid separation chamber is located at a greater radial distance from the axis of rotation than the first outlet. A suspension comprising a quantity of first particles is flowed into the inlet of the rotating fluid separation chamber, and a saturated fluidized bed of the first particles is formed within the fluid separation chamber in an area intermediate the inlet and the first outlet of the fluid separation chamber and adjacent the second outlet. A further quantity of the suspension comprising a quantity of the first particles is flowed into the inlet of the rotating fluid separation chamber while the fluidized bed of the first particles is simultaneously maintained, so that as additional suspension of the first particles is introduced into the fluidized bed, a quantity of the first particles flows through the second outlet and a portion of the liquid suspending the first particles flows out the first outlet.

In a further aspect of the method, concentration of the first particles may be obtained by alternatively flowing the suspension into the third port of the fluid separation chamber. Due to the G-forces to which the suspension is subjected, the first particles will separate from the suspending liquid and move toward the first port to exit therefrom. Simultaneously, the separated suspending liquid moves toward the second port to exit therefrom.

In another aspect of the disclosure, the flow rate of suspended particles into the fluid separation chamber is controlled. Additionally, once a desired amount of the first particles is collected through the second outlet, flow through the fluid separation chamber may be reversed to permit a collection through the inlet of the remaining suspended first particles that form the saturated fluidized bed.

In another aspect of the disclosure, the first particles are platelets, and the suspending liquid is plasma.

DETAILED DESCRIPTION

While the method and apparatus are described in the context of the continuous blood cell separation procedure and apparatus, it can equally well be used in a blood banking operation, in which whole blood is collected from a donor and then later further processed by centrifugation into its separate components.

A more detailed description of the method and apparatus in accordance with the present disclosure is set forth below. It should be understood that the description below of a specific device and method is intended to be exemplary, and not exhaustive of all possible variations or applications. Thus, the scope of the disclosure is not intended to be limiting, and should be understood to encompass variations or embodiments that would occur to persons of ordinary skill.

The embodiments of the present disclosure preferably include a blood component centrifuge such as the Amicus® separator and Alyx® separator referred to above. However, the specific details as to the centrifuge system are not material to the subject matter of the present disclosure, as the device and method disclosed herein may be advantageously used in a variety of different centrifuge devices that are commonly used to separate blood into its components.

Figure 1:
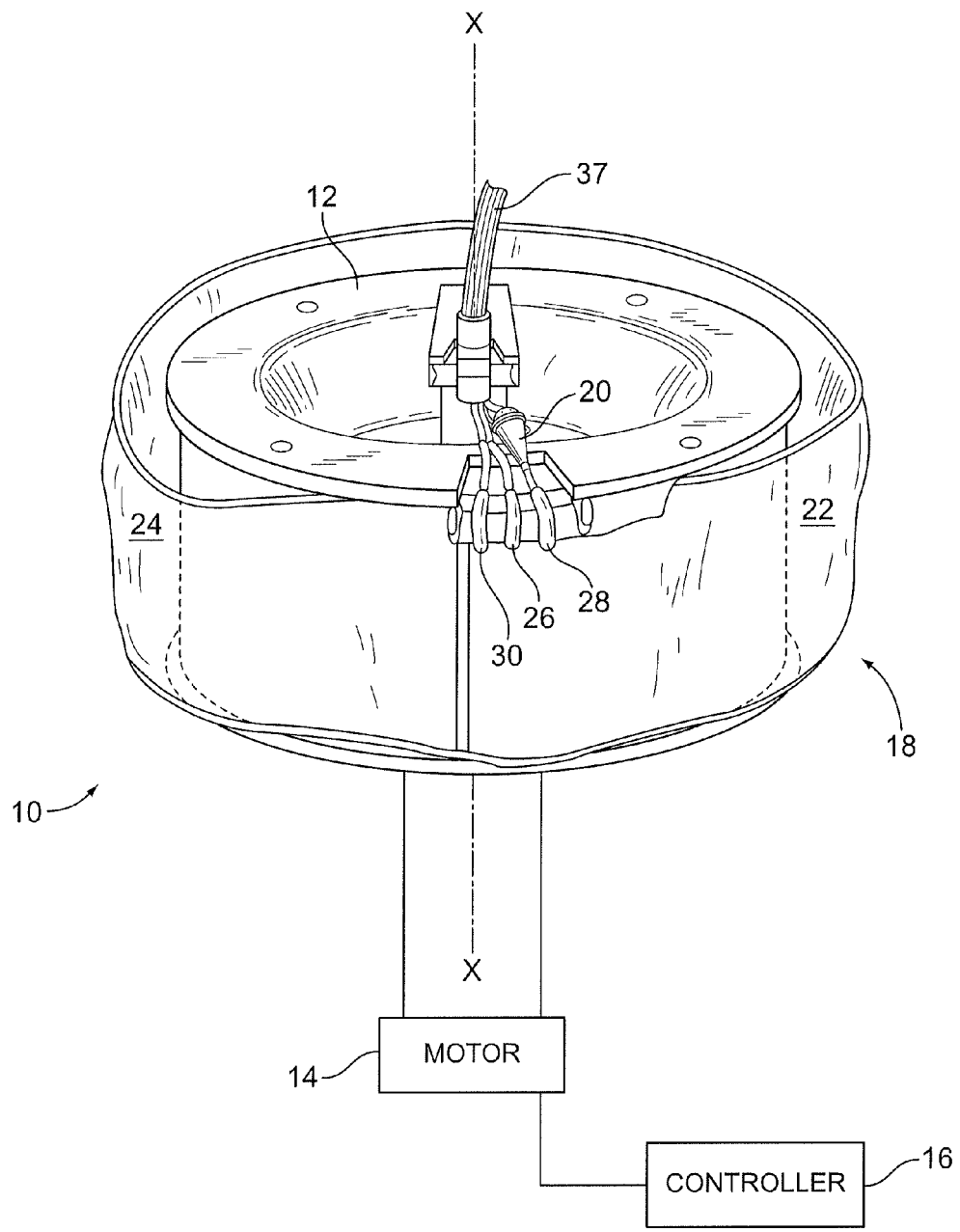
FIG. 1 is a partial schematic representation of a centrifuge apparatus including a single use blood processing chamber and a fluid suspension chamber in accordance with an embodiment of the present disclosure.

With reference to FIG. 1, there is seen a schematic representation of a portion of a centrifuge apparatus generally designated 10, having a rotor 12 that rotates about a axis of rotation X-X. The rotor 12 is rotated by a motor 14 which is controllable by a controller 16. A disposable blood processing chamber 18 is preferably mounted to the rotor 12, as is a secondary fluid separation chamber 20, which is secured generally along a radius of the rotor by suitable holder.

Figure 2:
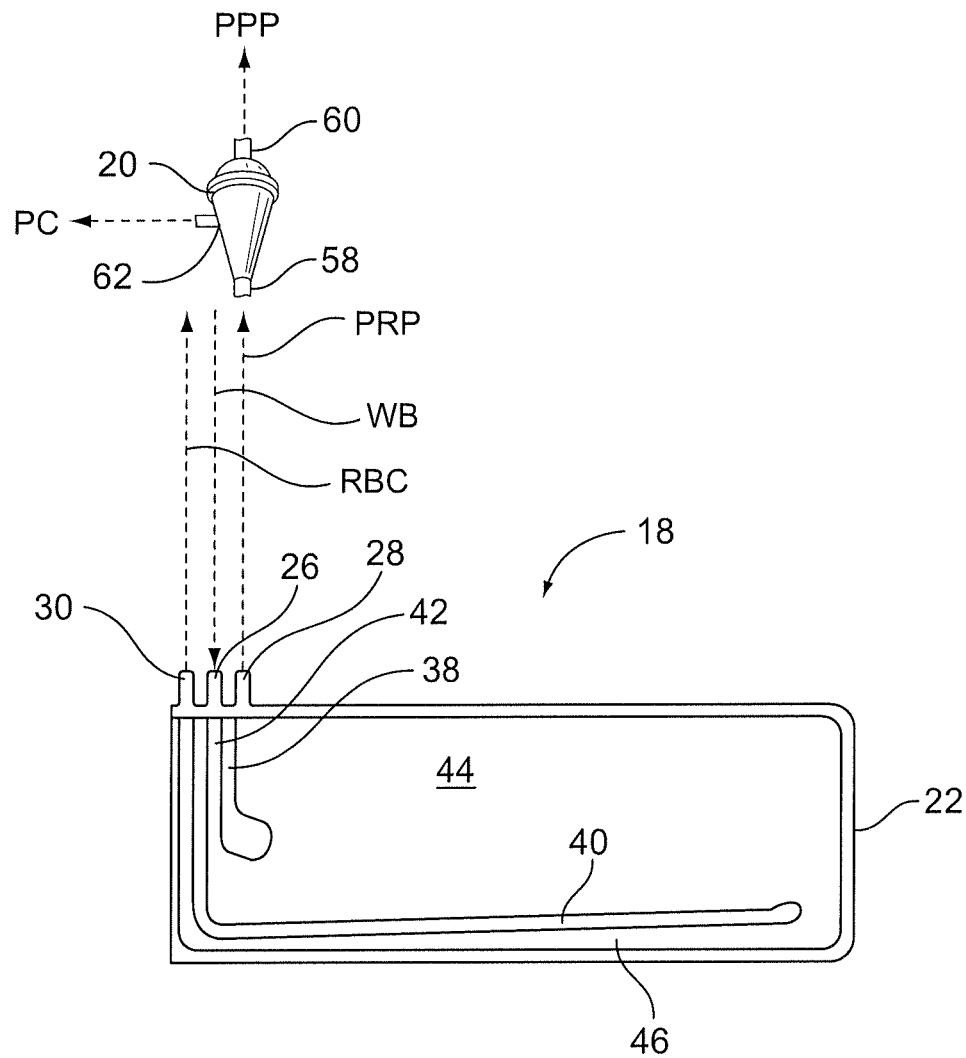
FIG. 2 is a plan view of the blood processing chamber shown in FIG. 1 out of association with the spool, including the fluid separation chamber.

The blood processing chamber 18 may be variously constructed so as to provide platelet-rich plasma (PRP) to the fluid separation chamber 20 for further concentration, and the present disclosure is not limited to use with any specific configuration for the blood processing chamber 18. A representative embodiment of a blood processing chamber suitable for use in connection with the systems and methods disclosed herein is shown in FIG. 2. As illustrated, the blood processing chamber 18 provides for processing with a first stage 22 that separates whole blood (WB) into red blood cells (RBC) and platelet-rich plasma (PRP). The blood processing chamber 18 includes ports 26, 28 and 30 arranged side by side along an edge of the chamber, with a tubing bundle or umbilicus 37 comprising the individual tubings attached to the ports. The tubings comprising the umbilicus 38 interconnect the first stage 22 and secondary separation chamber 20 with each other, and with pumps and other stationary components located outside the rotating components of the centrifuge.

More specifically, the blood processing chamber 18 includes a port 26 through which WB is conveyed into the first stage 22. Two ports 28, 30 respectively convey PRP and RBC out from the first stage, with the RBCs typically, but not necessarily, being returned to the donor and the PRP being conveyed into the secondary separation chamber 20.

The blood processing chamber 18 further includes a first interior seal 38 located between the PRP collection port 28 and the WB inlet port 26 and a second interior seal 40 between the WB inlet port 26 and the RBC collection port 30. The interior seals 38, 40 form a WB inlet passage 42 and a PRP collection region 44 in the first stage 22 of the blood processing chamber 18. The second seal 40 also forms an RBC collection passage 46 in the first stage. PRP exits the first stage 22 through port 28 and is pumped into the secondary separation chamber 20.

In keeping with one aspect of the disclosure, the platelet-rich plasma exiting the first stage 22 of the blood processing chamber 18 is further processed to obtain a platelet concentrate having a higher desired concentration of platelets.

Specifically, the platelet-rich plasma is processed through a secondary fluid separation chamber 20 that has a first port comprising an inlet 58 and a second port comprising a first outlet 60 spaced apart from the inlet 58. The cross sectional area of the separation chamber 20 varies in a direction generally transverse to a radius extending from the axis of rotation of the centrifuge, the cross sectional area varying between the inlet and the first outlet. As illustrated, the secondary separation chamber 20 comprises a first section adjacent the inlet 58 having a generally conical shape terminating in the maximum cross-sectional area of the chamber 20, and a second section adjacent the first outlet having a generally hemi-spherical shape. The fluid separation chamber 20 is mounted to the rotor 12 for rotation with the centrifuge so as to be located generally symmetrically along a radius extending from the axis of rotation of the centrifuge, with the inlet 58 located at a greater radial distance from the axis of rotation than the first outlet 60. The fluid separation chamber 20 further comprises a third port comprising a second outlet 62 radially intermediate the inlet 58 and the first outlet 60.

Figure 3:
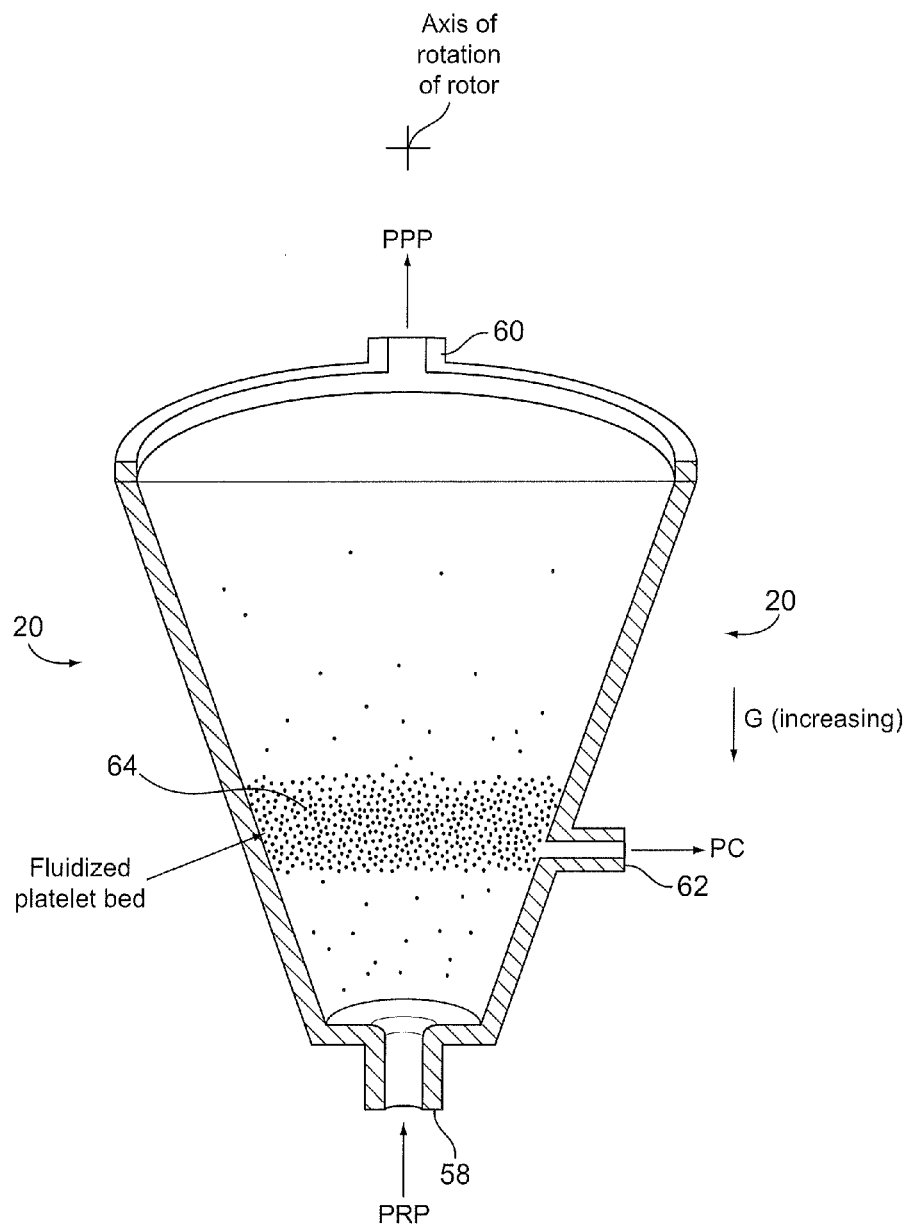
FIG. 3 is an enlarged cross-sectional view of a fluid separation chamber in accordance with the present disclosure.

In use, and with reference to FIG. 3, a cell batch having a first type of cell suspended in a liquid medium is introduced into the secondary fluid separation chamber 20, which is spinning synchronously with the rotor 12 of the centrifuge 10. The spinning of the fluid separation chamber 20 causes the lower density, slower sedimenting cells to move toward the first outlet 60 of the separation chamber 20, while the higher density, faster-sedimenting cells migrate toward the area of the chamber subject to the greatest centrifugal force, i.e., the inlet 20. The centrifugal force and the force generated by the fluid flow into the fluid separation chamber through the inlet 58 are balanced, so that the higher density, faster sedimenting cells form a fluidized bed 64 in an intermediate region of the fluid separation chamber. When additional fluid is flowed into the inlet 58 of the separation chamber, the higher density, faster-sedimenting cells in the additional fluid migrate into the fluidized bed 64, thus forcing some of the higher density cells out through the second outlet 62 of the separation chamber 20. Simultaneously, some of the lower density, slower-sedimenting cells will exit through the first outlet 60.

More specifically, PRP, which comprises platelets suspended in plasma, are removed from the first stage 22 of the blood processing chamber 18 and introduced into the secondary fluid separation chamber 20 so that the platelets form a saturated fluidized particle bed 64. The location of the fluidized bed 64 of platelets within the fluid separation chamber 20 establishes itself automatically, with its volume and location varying depending on the flow rate into the fluid separation chamber 20 and the centrifugal field created by rotation of the rotor 12. The controller maintains the rotational speed of the rotor to facilitate the formation of the saturated fluidized bed, and also preferably regulates a pump to convey further PC into the fluid separation chamber 20 at a predetermined flow rate. The plasma, being of lower density than the platelets, accumulates adjacent the first outlet 60. Once the fluidized bed 64 of platelets is formed, for each additional platelet entering the saturated bed 64 in the chamber 20, a platelet exits the fluidized bed 64 through the second outlet 62, with the additional plasma exiting through the first outlet 60.

Once the desired concentration of platelets is collected through the second outlet 62 of the separation chamber 20, fluid flow through the separation chamber 20 may be reversed, with PPP being pumped into the first outlet 60 of the separation chamber 20, to permit collection of any remaining platelets suspended in the fluidized bed 64 by driving the platelets back through the inlet 58 and into the second stage 24 of the blood processing chamber 18.

Figure 4:
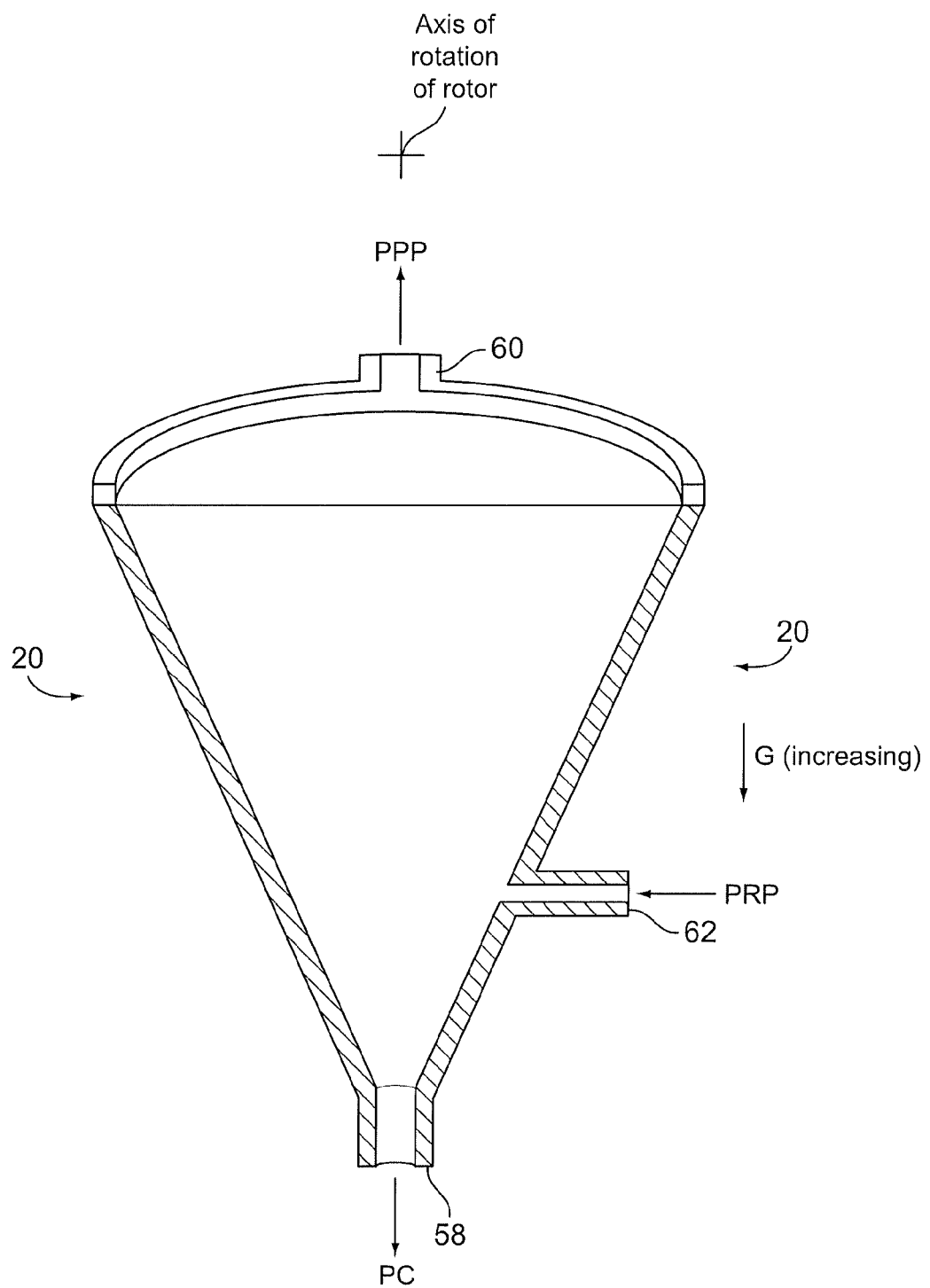
FIG. 4 is an enlarged cross-sectional view of an alternative embodiment for a fluid separation chamber in accordance with the present disclosure.

Alternatively, the fluid separation chamber 20 may also be used to obtain platelet concentrate without requiring the formation of a fluidized bed. Specifically, and as illustrated in FIG. 4, platelet-rich plasma may be introduced into the intermediate port 62 of the separation chamber 20 while it is rotating in unison with the centrifuge. The G-forces to which the PRP is subjected will cause separation of the platelets from the plasma, with the separated platelets moving toward and out of the high-G port 58, while plasma moves toward and exits the low-G port 60.

In order to insure that separated platelets are funneled towards the port 58 without obstruction, the separation chamber 20 is shaped so that no horizontal ledge is created adjacent the port 58 on which platelets could be accumulated by the G-forces pushing them towards the port 58.

Alternatively, the separation chamber 20 could be cylindrical in shape with a cone-shaped bottom section (as shown in FIG. 4). Further, it may be necessary to direct the flow from port 62 in a manner that will not introduce turbulent flow in the separation chamber 20 that could possibly impede the separation of the platelets.

Thus, an improved method and apparatus for concentrating platelets from platelet-rich plasma has been disclosed. The description provided above is intended for illustrative purposes only, and is not intended to limit the scope of the disclosure to any particular embodiment described herein. As would be obvious to those skilled in the art, changes and modifications may be made without departing from the disclosure in its broader aspects. Thus, the scope is to be as set forth in the following claims.

The invention claimed is:

1. An apparatus for use with a centrifugal cellular separation device comprising a rotor rotatable about an axis of rotation, the apparatus comprising:
    a fluid separation chamber having an interior with a first port and a second port spaced apart from the first port along an axis of the chamber and a cross sectional area generally transverse to the axis of the chamber that varies between the first port and the second port;
    the fluid separation chamber being configured to be mounted to the rotor so as to be rotatable therewith with the first port located at a greater radial distance from the axis of rotation than the second port; and
    the fluid separation chamber further comprising a third port radially intermediate the first port and the second port, each of the first, second and third ports defining an opening on the interior of the chamber, with the opening of the third port being intermediate the openings of the first and second ports.

2. The apparatus of claim 1 wherein the cross sectional area of the chamber has a maximum cross sectional area at a radial location between the first port and second port.

3. The apparatus of claim 1 where the fluid separation chamber comprises a generally conical shape between the first port and the location of the maximum cross-sectional area.

4. A centrifugal cellular separation device comprising:
    a rotor rotatable about an axis of rotation; and
    the apparatus of claim 1 removably secured to the rotor so as to be rotatable therewith, with the first port and the second port aligned generally along a radius of the rotor through the axis of rotation of the rotor, the second port being positioned along the radius between the first port and the axis of rotation.

5. The apparatus of claim 4 wherein the rotor is durable and reusable and apparatus is disposable.

* * * * *